US005273520A

United States Patent [19]

Rebmann

[11] Patent Number: 5,273,520

[45] Date of Patent: Dec. 28, 1993

[54] MOBILIZING SPLINT WITH REVERSIBLE MOTORIZATION ASSEMBLY

[75] Inventor: Georges M. E. Rebmann, Charleville Mezieres, France

[73] Assignee: Copagnie Generale de Materiel Orthopedique, Tournes, France

[21] Appl. No.: 757,844

[22] Filed: Sep. 11, 1991

[30] Foreign Application Priority Data

Sep. 14, 1990 [FR] France ............................... 90 11585

[51] Int. Cl.[5] ........................... A61F 5/00; A61H 1/02

[52] U.S. Cl. ..................................... 602/5; 128/25 R; 128/25 B

[58] Field of Search .................. 128/87 R, 82.1, 84 R, 128/83, 88, 89 R, 25 R, 25 B; 606/57, 105; 602/23, 24, 25, 26, 27, 39, 40

[56] References Cited

U.S. PATENT DOCUMENTS

| | | | |
|---|---|---|---|
| 1,904,942 | 4/1933 | Heigl | 128/84 |
| 2,052,990 | 9/1936 | Siebrandt | 128/88 |
| 2,486,687 | 11/1949 | Svaetichin | 128/88 |
| 2,515,590 | 7/1950 | Chaffin | 128/84 R |
| 3,066,322 | 12/1962 | Derby | 128/88 |
| 3,419,002 | 12/1968 | Santosus | 128/88 |
| 3,472,224 | 10/1969 | Ewerwahn | 128/87 R |
| 3,651,803 | 3/1972 | Bimler | 128/88 |
| 4,336,796 | 6/1982 | Andrew | 128/87 R |
| 4,603,687 | 8/1986 | Greenwood | 128/25 R |
| 4,930,497 | 6/1990 | Saringer | 128/25 R |
| 5,025,802 | 6/1991 | Laico | 128/84 R |
| 5,056,535 | 10/1991 | Bonnell | 128/84 R |

FOREIGN PATENT DOCUMENTS

| | | |
|---|---|---|
| 3609777A1 | 9/1987 | Fed. Rep. of Germany . |
| 3727186A1 | 2/1989 | Fed. Rep. of Germany . |

*Primary Examiner*—Michael A. Brown
*Attorney, Agent, or Firm*—Pravel, Hewitt, Kimball & Krieger

[57] ABSTRACT

An orthopaedic reeducation splint for the passive mobilisation of a lower limb, which includes a housing (15) fastened to the structure (7) and mounted rotatably on the joint pin (8) which is fixed to the support (5). A large toothed ring (25) is immobilised on the pin, and an electric motor (3) with two directions of rotation is mounted in the housing. A reduction mechanism (32) is mounted in the housing and interposed between the electric motor and the large toothed ring which it engages.

6 Claims, 3 Drawing Sheets

MOBILIZING SPLINT WITH REVERSIBLE MOTORIZATION ASSEMBLY

RELATED APPLICATIONS

This application claims priority from French Patent No. 90 11585 filed on Sep. 14, 1990.

BACKGROUND OF THE INVENTION

The present invention relates to equipment for the functional reeducation and orthopaedic treatment of the joints of the limbs of the human body.

The present invention is concerned more particularly with splints, said to be movable, in comparison with appliances of fixed structure which allow only the support or posture of a traumatised limb.

Movable splints known hitherto consist mainly of a supporting means, on which is mounted by means of a joint pin a structure, said to be movable, capable of receiving and supporting at least partially the limb to be mobilised, for the purpose of the functional reeducation of one of the joints of this limb. Means are provided, of course, between the movable structure and the limb, to ensure support and retention under requisite conditions of functionality.

To perform a passive mobilisation function, splints of the above-mentioned type have been equipped with a motorisation assembly which is generally interposed between the movable structure and the supporting means. Such a motorisation assembly provided in various forms usually brings into operation an electric motor responsible for actuating a screw jack, so that, as a result of either of its rotations, it can control the bending and stretching of the movable structure in relation to the support.

Splints of the above-mentioned type are commonly used either in the domestic environment or in the hospital environment and can be considered as making it possible to ensure an acceptable reeducation function.

It was found, however, that because of the arrangement of the motorisation assembly it was impossible to obtain a constant driving torque, whatever the bending/stretching angle of the movable structure in relation to the supporting means, and a speed of angular movement constant over the entire attainable bending/stretching range. Variations in the driving torque and in the speed must be considered as scarcely favorable, if not unfavorable, to functional reeducation under ideal conditions, in view of the fact that the mobilised joint is subjected to variable and excessively high loads in terms of speed or torque periodically and outside the reeducational load schedules which have to be imposed on it.

Furthermore, it was also found that the arrangement involving interposing the motorisation assembly between the movable structure and the supporting means resulted, for the same reasons of variations in torque and speed, in a transmission efficiency, if not poor, at least nowhere near the best possible, and that it was consequently necessary to oversize the motorisation assembly by adopting a motor of a power higher than that required.

A direct result of this constraint is the higher cost price and a bulk which sometimes opposes the mounting of such means on small-size splints, such as those for the direct reeducation of the wrist and ankle.

The object of the invention is to remedy the above-mentioned problem by providing a new reversible motorisation assembly of small bulk, designed to be quickly adaptable to all types of movable reeducation structures and making it possible to impose on at least one of the segments of a simple or complex movable structure a relatively constant speed of angular movement and a constant driving torque, whatever the bending/stretching angle of said segment.

The above-mentioned means make it possible to carry out reeducational work of the highest quality and to construct reeducational splints at lower cost than that of current splints.

To achieve the above-mentioned aims, the motorisation assembly according to the invention is characterised in that it comprises:

a housing fastened to the structure and mounted rotatably on the joint pin which is fixed to the support;

a large toothed ring immobilised on the pin;

an electric motor with two directions of rotation mounted in the housing;

a reduction mechanism mounted in the housing and interposed between the electric motor and the large toothed ring which it engages.

Another subject of the invention is a splint for mobilising at least one joint of a lower limb, comprising a movable structure on which is attached the motorisation assembly likewise connected to the support of said structure.

BRIEF DESCRIPTION OF THE DRAWINGS

Various other characteristics emerge from the description given below with reference to the accompanying drawings which illustrate one embodiment of the subject of the invention by way of non-limiting example.

DETAILED DESCRIPTION OF AN EXEMPLARY EMBODIMENT

The subject of the invention, designated by the reference 1, is a reversible motorisation assembly attachable to a splint 2 designed to allow the passive mobilisation of at least one joint of a limb. By mobilisating splint is means any articulated system designated for the passive mobilisation of a joint between two segments of a limb of the human body, for the purpose of ensuring a functional readaptation or reeducation of said joint.

Figure 1:
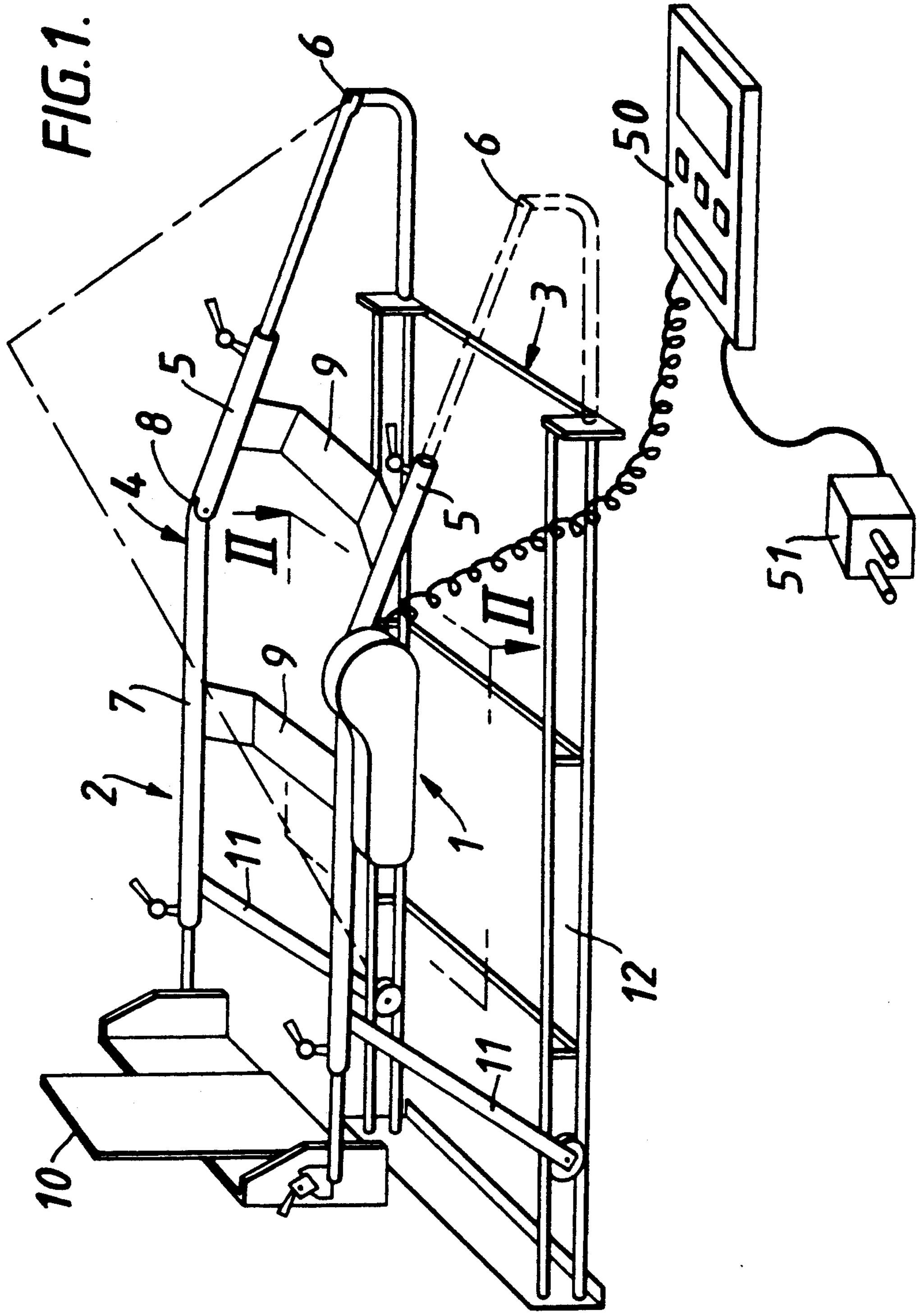
FIG. 1 is a diagrammatic view illustrating the use of the subject of the invention on one type of mobilising splint.

As an example, FIG. 1 shows a splint 2 designed for the passive mobilisation of a lower limb. The splint 2 comprises a base 3 or the like intended for resting on a bearing plane or indeed directly on the mattress of a bed. The base 3 supports an articulated assembly 4 comprising a first support 5, called a crural cradle, which is articulated on the base 3 by means of pins 6. The pins 6 embody the coxofemoral joint, the position of which can, if appropriate, be made adjustable. Furthermore, the articulated assembly 4 comprises a second support 7, called a tibial cradle, articulated on the crural cradle 5 by means of pins 8. The cradles 5 and 7 consist of spars, if appropriate adjustable, connected to one another by means of spacers 9 supporting suspension fittings, such as hammocks.

In the illustration according to FIG. 1, the tibial segment 7 is equipped at the end with a foot-rest plate 10 which, if need be, can be made articulated. The tibial segment 7 is supported with the aid of rolling members 11 by a guide track 12 which is defined by the base 3.

The motorisation assembly 1 according to the invention is intended for moving the articulated assembly 4 from a stretched position, as shown in FIG. 1, into a bending position, such as that represented by dot-and-dash lines, in which the articulated system 4 has undergone simultaneous pivoting on the pins 6 and 8.

According to the invention, the motorisation assembly 1 is designed so that it can be attached in parallel with the articulated structure 4, in order to actuate the movable structure in terms of bending and stretching directly by means of the pivot 8.

The motorisation assembly according to the invention is to be considered as capable, depending on the type of mobilising splint, of controlling the relative pivoting of all movable structures in relation to a pivot pin carried by any support. This could apply to the pivoting of the crural segment 6 on the pin 6 in relation to the base 3 or also of an articulated structure responsible for the mobilisation of the scapulohumeral joint in relation to a fixed upright.

Within the meaning of the invention, therefore, the motorisation assembly is intended to be quickly and easily attached laterally to a structure articulated in relation to its support, so as to control the pivoting of this structure by acting directly by reaction on the pivot pin of this structure.

According to FIGS. 2 to 5, the motorisation assembly 1 comprises a housing 15 fixed to the movable structure to be mobilised, such as consists of the tibial segment 7, with a view to the use illustrated in FIG. 1. Moreover, the housing 15 is mounted with the possibility of rotation on the pivot pin, such as 8, which is fixed to the support consisting, in the present use, of the crural segment 5.

The articulated connection between the segment 7 and the support 5 brings into operation a fork 16 which is located on the support 5 and through which passes the pivot pin 8 which is immobilised angularly and axially in this fork by all suitable means, particularly by dowels 17. The pin 8 carries within the fork 16 a tab 18 which is fixed to the structure 7 and the rotation for which is ensured by the interposition of a rolling bearing 19.

The pivot pin 8 possesses laterally an extension 8*a*, on which the housing 1 is mounted so as to be freely rotatable. For this purpose, the housing 1 consists of two panels 20 and 21 extending parallel to one another, at the same time being fixed together by means of spacer walls, such as 22. The panel 20 is fastened to the structure 7 by all suitable means, whilst the pivoting on the extension 8*a* brings into operation collars or plain bearings 23 and 24 carried by the panels 20 and 21. Moreover, the extension 8*a* supports between the panels 20 and 21 a large toothed ring 25 which is immobilized angularly and axially, particularly by means of a dowel 26.

The housing 15 carries a reversible electric motor 30, for example, fastened to the wall 22, in such a way that its output shaft 31 is directed toward the extension 8*a*. The motor 30 is completed by a reduction mechanism 32 interposed between the output shaft 31 and the large ring 25. In an exemplary embodiment, the reduction mechanism 32 brings into operation two stepdown stages 33 and 34 which must be considered as corresponding to one exemplary embodiment only. In fact, in practice, the mechanism 32 could consist of a single reduction stage.

The stage 33 comprises a primary shaft 35 mounted by means of bearings 36 on the panels 20 and 21. The primary shaft 35 carries a toothed pinion 37 interacting with a bevel pinion 38 carries by the shaft 31. The pinions 37 and 38 constitute a bevel gear which could be replaced by all transmission arrangements suitable for or emerging from a different installation of the motor member 30.

The primary shaft 35 carries a driving pinion 39 which is a component of the train 33, the driven pinion 40 of which is carried via a shaft, called secondary 41, mounted on the panels 20 and 21 by means of bearings 42. The secondary shaft 41 carries a pinion 43, called a pinion engaging the ring 25, with which it meshes, in the manner of an epicyclic gear train. It must, of course, be considered that, depending on the internal structural formation of the various component elements of the motorisation assembly, the interaction between the engaging pinion 43 and the ring 25 which are components of the second train 34 could bring into operation a train of the hypocycloidal type.

The electric motor is fed from a suitable source of electrical energy by means of a control box 50, if appropriate with programming. In the example according to FIG. 1, the box 50 is interposed ahead of a plug 51 making it possible to feed the motorisation assembly from an electrical energy distribution circuit, such as the mains. Equivalent arrangements on the basis of accumulator batteries, incorporated or not, could also be considered.

The box 50 is designed to allow the control, programmed or not, of the feed of the motor 30 in one direction or the other and/or successively and over adjustable angular ranges, indeed also at likewise adjustable angular speeds.

The above-described reversible motorisation assembly functions as follows.

Figure 2:
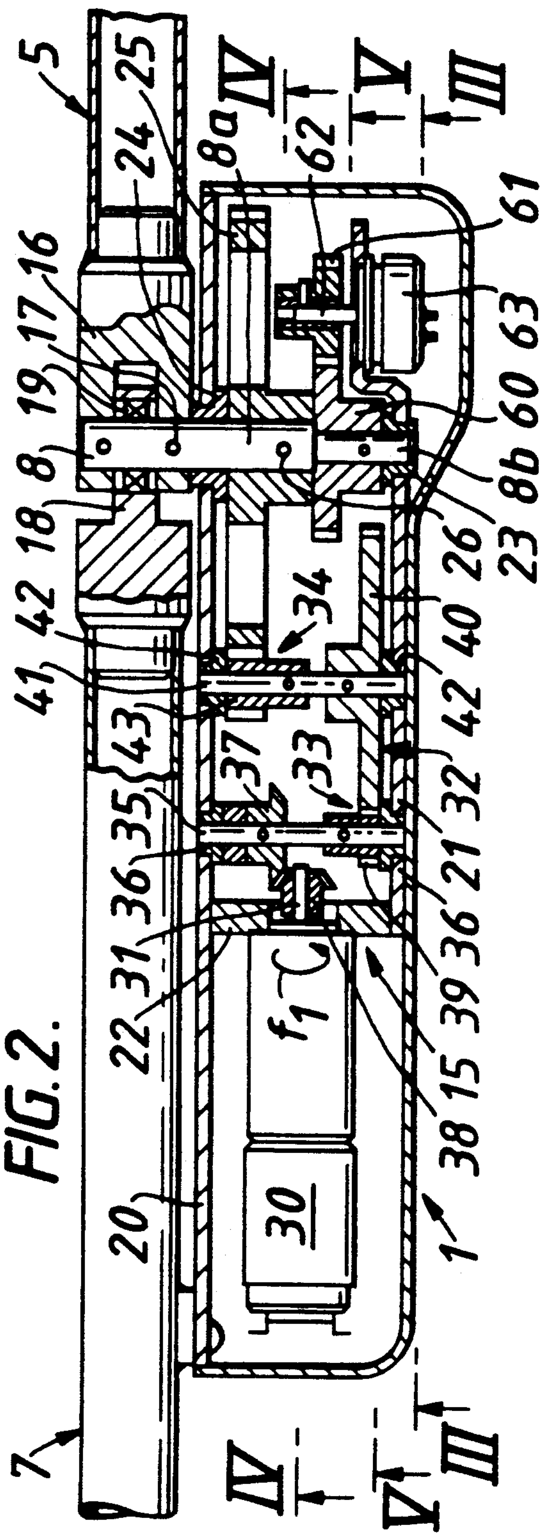
FIG. 2 is a sectional elevation view taken on a larger scale substantially in the plane II—II of FIG. 1.
Figure 3:
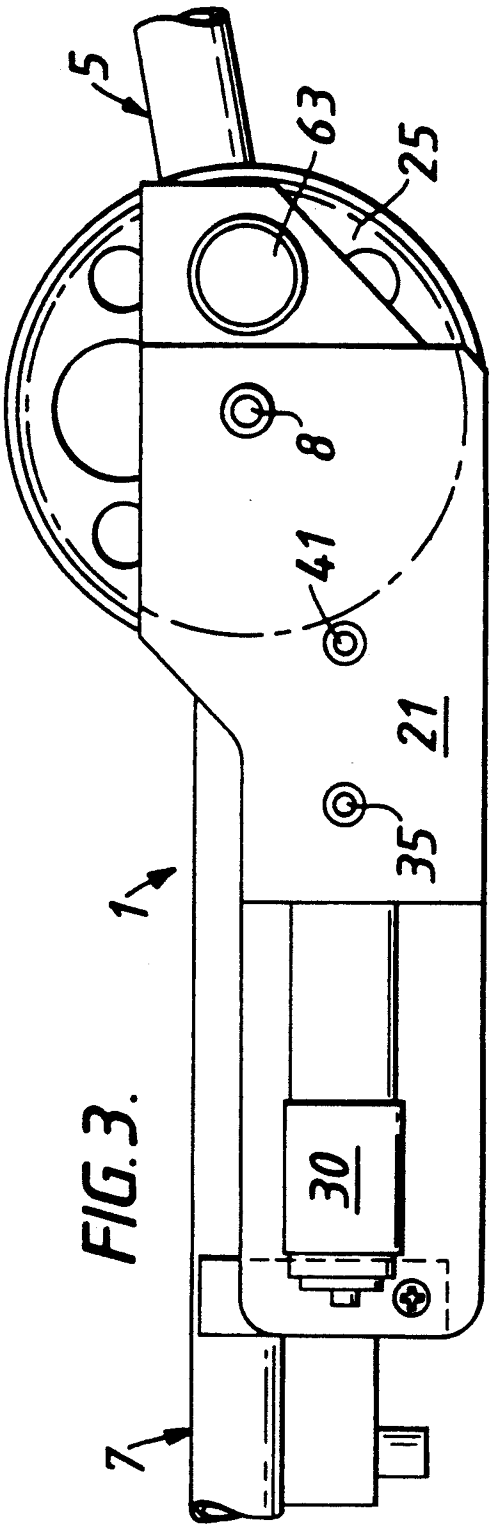
FIGS. 3 to 5 are sections taken along the lines III—III to V—V of FIG. 2.
Figure 4:
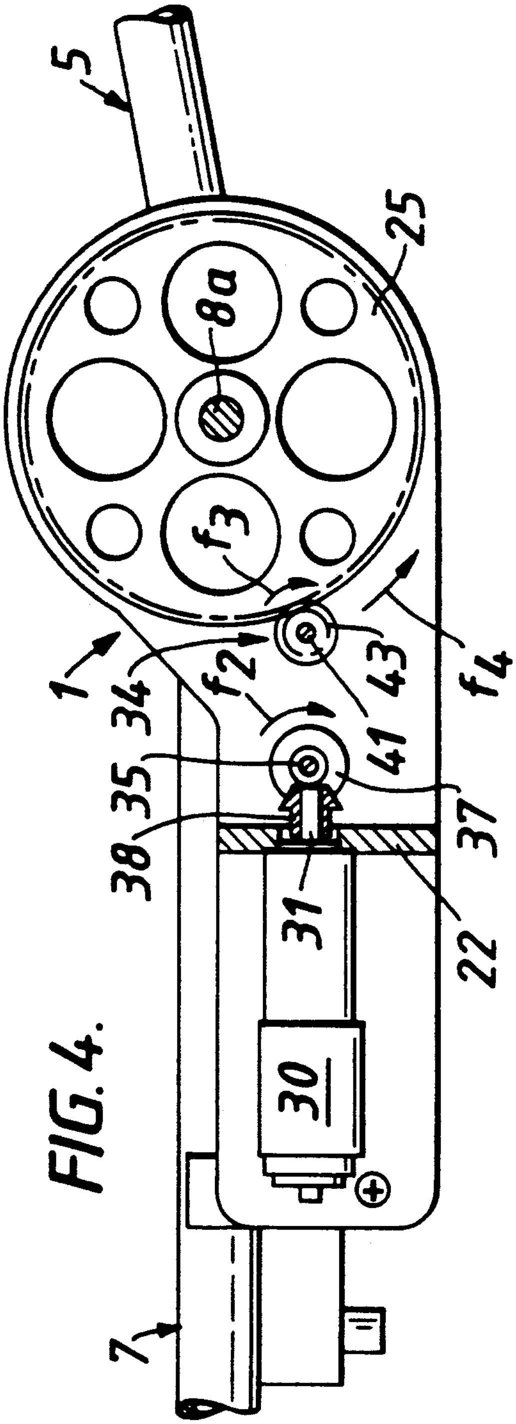
Figure 5:
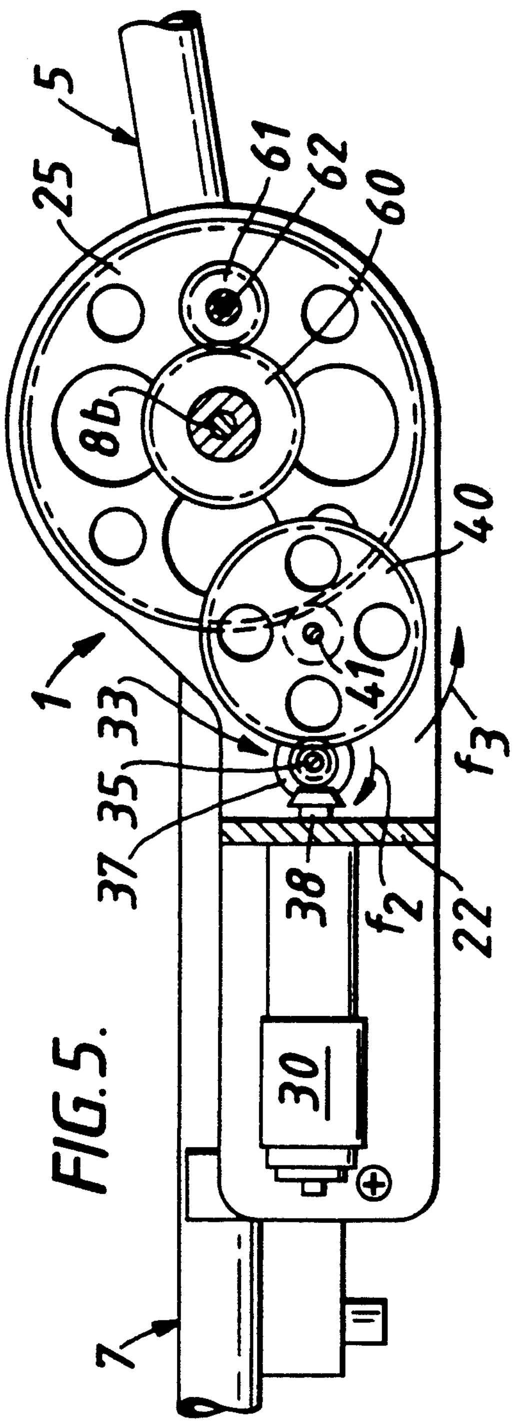

From a stretched position, as illustrated in the drawings, the motor 30 is fed in the appropriate direction to rotate the output shaft in the direction of the arrow $f_1$ (FIG. 2). This rotation is transmitted by the pinion 37 to the primary shaft 35 which is driven in the direction of the arrow $f_2$ (FIGS. 4 and 5). The rotation of the driving pinion 39 causes the driven pinion 40 of the stage 34 to rotate in the direction of the arrow $f_3$ (FIG. 5), in order to control the rotation of the engaging pinion 43 in the same direction (FIG. 4).

Because the large ring 25 is immobilised on the extension 8*a*, itself keyed angularly on the support 5, the drive of the pinion 43 in rotation results in a planetary revolution of the latter in the direction of the arrow $f_4$ (FIG. 4). This rotation is transmitted to the panels 20 and 21 of the housing 15 which drives the articulated structure 7, that is to say the tibial segment, in the corresponding direction, by reaction and where the structure according to FIG. 1 is concerned, the articulated assembly 4 is subjected to bending stress by pivoting on the pin 8.

As emerges from the foregoing, the lateral attachment to the motorisation assembly allows a saving of weight and of bulk. Moreover, the assembly 1 acts directly by a reaction effect on the pivot pin 8 responsible for the angular movement of the articulated structure 7 in relation to its support 5. Thus, the torque and speed can be applied in a constant manner, whatever the angular bending/stretching range, in order by passive mobilisation to cause a joint to be reeducated to work under the best possible conditions.

The use of one possible constant speed and of a constant torque makes it possible to design the motorisation assembly so as to give it just the working power necessary, with the result that it becomes possible to reduce the bulk and the power of the motor 30.

The motorisation assembly can therefore be produced at lower cost than that of current solutions.

According to a secondary arrangement of the invention, there is mounted on the end part of the extension 8*a*, for example the end part 8*b*, a toothed pinion 60 permanently meshing with a wheel 61 mounted on the output shaft 62 of a position sensor 63 carried by the panel 21. The sensor 63, of the potentiometric type or of the electric incrementation or absolute coder type, is thus driven in rotation in accompaniment with the pivoting of the structure 7 and can assess the angular amplitude covered, in order to supply the control box 50 with the actual position of the mechanism in terms of amplitude. This information makes it possible and, if necessary, make a correction. It is thus possible to control the position and the speed of the mobilisation assembly perfectly.

The invention is not limited to the example described and illustrated, for various modifications can be made to is, without departing from its scope.

I claim:

1. A passive mobilization splint comprising:

a base frame, a first support pivotally attached at one end to said base frame;

a second support rotatably supported at one end by said base frame and pivotally attached at said other end to said first support; and a reversible motor assembly fixedly attached to said second support and pivotally connected to said pivotal attachment of said first and second supports wherein the placement of said reversible motor assembly permits the full extension of said first and second supports in horizontal parallel alignment, said assembly having:

a housing attached to said second support and having a longitudinal axis substantially parallel with a longitudinal axis of said support, a large toothed ring fixedly mounted to said pivotal attachment of said first and second supports, an electric motor with two directions of rotation mounted within said housing, and means for reducing the angular velocity of said large tooth ring, said means being mounted in said housing between said electric motor and said large tooth ring,

2. The passive mobilization splint according to claim 1 wherein said reducing means includes at least one step-down stage.

3. The passive mobilization splint according to claim 2 wherein said reducing means comprises a first shaft mounted within bearings supported by said housing;

an output shaft extending from said electric motor;

a first pinion mounted on said first shaft for rotatable angular movement with said output shaft; and a second pinion mounted on said first shaft at the opposite end from said first pinion, said second pinion being drivably engageable with said large tooth ring.

4. The passive mobilization splint according to claim 1 wherein said first support comprises a crural cradle for the mobilization of a lower limb; said second support comprises a tibial cradle pivotally mountable to said base; and a guide and rolling track articulatably attached to said tibial cradle on which said housing of said reversible motor assembly is fastened.

5. The passive mobilization splint according to claim 1 wherein said reversible motor assembly further comprises a position sensor to assess the angular movement of said first support relative to said second support.

6. The passive mobilization splint according to claim 5 wherein said splint further comprises a control box for controlling the operation of said electric motor based on signals transmitted from said sensor.

* * * * *